(12) United States Patent
Macossay-Torres

(10) Patent No.: US 8,142,501 B2
(45) Date of Patent: Mar. 27, 2012

(54) ARTIFICIAL LIGAMENTS AND TENDONS COMPRISING MULTIFILAMENTS AND NANOFIBERS AND METHODS FOR MAKING

(75) Inventor: Javier Macossay-Torres, Edinburg, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 191 days.

(21) Appl. No.: 12/427,407

(22) Filed: Apr. 21, 2009

(65) Prior Publication Data

US 2009/0306775 A1 Dec. 10, 2009

Related U.S. Application Data

(60) Provisional application No. 61/046,739, filed on Apr. 21, 2008.

(51) Int. Cl.
*A61F 2/08* (2006.01)
(52) U.S. Cl. ..................................... 623/13.2
(58) Field of Classification Search ....... 623/13.11–13.2
See application file for complete search history.

(56) References Cited

U.S. PATENT DOCUMENTS

| | | | | |
|---|---|---|---|---|
| 1,975,504 A | 10/1934 | Formhals | | 264/10 |
| 2,160,962 A | 6/1939 | Formhals | | 264/10 |
| 2,187,306 A | 1/1940 | Formhals | | 428/375 |
| 2,323,025 A | 6/1943 | Formhals | | 264/10 |
| 2,349,950 A | 5/1944 | Formhals | | 264/10 |
| 3,176,316 A | 4/1965 | Bodell | | 623/13.19 |
| 4,246,660 A | 1/1981 | Wevers | | 623/13.13 |
| 4,584,722 A | 4/1986 | Levy et al. | | 623/13.15 |
| 4,932,972 A | 6/1990 | Dunn et al. | | 623/13.19 |
| 4,955,910 A | 9/1990 | Bolesky | | 623/13.13 |
| 5,356,435 A | 10/1994 | Thein | | 606/232 |
| 6,165,217 A * | 12/2000 | Hayes | | 623/11.11 |
| 6,382,526 B1 | 5/2002 | Reneker et al. | | 239/294 |
| 6,569,526 B2 * | 5/2003 | Rieder et al. | | 428/397 |
| 6,616,694 B1 | 9/2003 | Hart | | 623/13.14 |
| 6,764,513 B1 | 7/2004 | Dowling | | 623/13.14 |
| 6,863,969 B2 * | 3/2005 | Rieder et al. | | 428/294.7 |
| 7,235,295 B2 | 6/2007 | Laurencin et al. | | 428/364 |
| 2006/0030942 A1 * | 2/2006 | Vanderby et al. | | 623/13.17 |
| 2008/0286329 A1 * | 11/2008 | Campbell et al. | | 424/423 |
| 2009/0099600 A1 | 4/2009 | Moore et al. | | 606/246 |
| 2010/0047309 A1 * | 2/2010 | Lu et al. | | 424/423 |
| 2010/0106233 A1 * | 4/2010 | Grant et al. | | 623/1.1 |

OTHER PUBLICATIONS

Amis and Kempson, "Failure mechanisms of polyester fiber anterior cruciate ligament implants: A human retrieval and laboratory study," *J. Biomed. Mater. Res.*, 48:534-539, 1999.

Amstutz et al., "Reconstruction of the canine Achilles and patellar tendons using dacron mesh silicone prosthesis. I. Clinical and biocompatibility evaluation," *J. Biomed. Mater. Res.*, 10:47-59, 1976.

Andrews et al., "Technology of electrostatic spinning for the production of polyurethane tissue engineering scaffolds," *Polym. Int.*, 57:203-210, 2008.

Azangwe et al., "Preliminary comparison of the rupture of human and rabbit anterior cruciate ligaments," *Clin. Biomechanics*, 16:913-917, 2001.

(Continued)

*Primary Examiner* — Suzette J Gherbi
(74) *Attorney, Agent, or Firm* — Fulbright & Jaworski

(57) ABSTRACT

Prosthetic ligaments and tendons comprising ligament- or tendon-mimicking nanofibers and methods of making such nanofibers and prosthetic ligaments and tendons.

16 Claims, 6 Drawing Sheets

OTHER PUBLICATIONS

Bashur et al., "Effect of fiber diameter and orientation on fibroblast morphology and proliferation on electrospun poly(D,L-lactic-co-glycolic acid) meshes," *Biomaterials*, 27:5681-5688, 2006.

Baskaran et al., "Noncovalent and nonspecific molecular interactions of polymers with multiwalled carbon nanotubes," *Chem. Mater.*, 17:3389-3397, 2005.

Boretos, "Past, present and future role of polyurethanes for surgical implants," *Pure & Appl. Chem.*, 52:1851-1855, 1980.

Brandrup and Immergut, In: *Polymer Handbook*, John Wiley and Sons Inc., USA, V1-V87, 1975.

Chen et al., "Studies on segmented polyetherurethane for biomedical application: effects of composition and hard-segment content on biocompatibility," *J. Biomed. Mater. Res.*, 41:533-48, 1998.

Christenson et al., "Poly(carbonate urethane) and poly(ether urethane) biodegradation: in vivo studies," *J. Biomed. Mater. Res.*, 69:407-416, 2004.

Ciccone et al., "Structural properties of lateral collateral ligament reconstruction at the fibular head," *Am. J. Sports Med.*, 34:24-28, 2006.

Dauner, "Centrifuge Spinning—an economic alternative to electrospinning," NanoEurope Conference 2006, Sep. 14, 2006.

De Santis et al., "Continuous fibre reinforced polymers as connective tissue replacement," *Comp. Sci. & Tech.*, 64:861-871, 2004.

Demczyk et al., "Direct mechanical measurement of the tensile strength and elastic modulus of multiwalled carbon nanotubes," *Materials Science and Engineering A*, 334:173-178, 2002.

Demir et al., "Electrospinning of polyurethane fibers," *Polymer*, 43:3303-3309, 2002.

Ding et al., "Electrospun nanofibers membranes coated quartz crystal muicrobalance as gas sensro $NH_3$ detection," *Sens. Actuator B*, 101:373-380, 2004.

Doroski et al., "Techniques for biological characterization of tissue-engineered tendon and ligament," *Biomaterials*, 28:187-202, 2007.

Dror et al., "Carbon nanotubes embedded in oriented polymer nanofibers by electrospinning," *Langmuir*, 19:7012-7020, 2003.

Freeman et al., "Tissue engineering of the anterior cruciate ligament using a braid-twist scaffold design," *J. Biomech.*, 40:2029-2036, 2007.

Fujii et al., "Reconstruction of neglected Achilles tendon rupture with Leeds-Keio artificial ligament," *The Foot*, 7:139-143, 1997.

Fujishiro et al., "Reconstruction of the iliofemoral ligament with an artificial ligament for recurrent anterior dislocation of total hip arthroplasty," *J. Arthroplasty*, 18:524-527,2003.

Gogolewski, "Leading contribution: selected topics in biomedical polyurethans. A review," *Colloid Polym. Sci*, 267:757-785, 1989.

Gong et al., "Surfactant-assisted processing of carbon nanotube/polymer composites," *Chem. Mater.*, 12:1049-1052, 2000.

Guidoin et al., "Analysis of retrieved polymer fiber based replacements for the ACL," *Biomaterials*, 21:2461-2474, 2000.

Huang et al., "A review on polymer nanofibers by electrospinning and their applications in nanocomposites," *Comp. Sci. & Tech.*, 63:2223-2253, 2003.

Hukins et al., "Biomaterials: defining the mechanical properties of natural tissues and selection of replacement materials," *J. Mater. Chem.*, 9:629-636, 1999.

Jadeja et al., "Patterns of failure with time of an artificial scaffold class ligament used for reconstruction of the human anterior cruciate ligament," *The Knee*, 14:439-442, 2007.

Jeon et al., "Chronic acromioclavicular separation: the medium term results of coracoclavicular ligament reconstruction using braided polyester prosthetic ligament," *Injury*, 38:1247-1253, 2007.

Kenawy et al., "Release of tetracycline hydrochloride from electrospun poly(ethylene-co-vinylacetate), poly(lactic acid), and a blend," *J. Control Release*, 81:57-64, 2002.

Kessick and Tepper, "Electrospun polymer composite fiber arrays for the detection and identification of volatile organic compounds," *Sens. Actuator B*, 117:205-210, 2006.

Laurencin and Freeman, "Ligament tissue engineering: an evolutionary materials science approach," *Biomaterials*, 26:7530-7536, 2005.

Lavoie et al., "Patient satisfaction needs as related to knee stability and objective findings after ACL reconstruction using the LARS artificial ligament," *The Knee*, 7:157-163, 2000.

Lee et al., "Nanofiber alignment and direction of mechanical strain affect the ECM production of human ACL fibroblast," *Biomaterials*, 26:1261-1270, 2005.

Lee et al., "The change of bead morphology formed on electrospun polystyrene fibers," *Polymer*, 44:4029-4034, 2003.

Li and Xia, "Electrospinning of nanofibers: reinventing the wheel?" *Adv. Mater.*, 16:1151-1170, 2004.

MacDiarmid et al., "Electrostatically-generated nanofibers of electronic polymers," *Synthetic Metals*, 119:27-30, 2001.

Macossay et al., "Electrospun fibers from poly(methyl methacrylate)/vapor grown carbon nanofibers," *Polym. Adv. Technol.*, 17:391-394, 2006.

Margevicius et al., "Identification and distribution of synthetic ligament wear particles in sheep," *J. Biomed, Mater. Res.*, 31:319-328, 1996.

Matarredona et al., "Dispersion of single-walled carbon nanotubes in aqueous solutions of the anionic surfactant NaDDBS," *J. Phys. Chem. B*, 107:13357-13367, 2003.

Mathur et al., "In vivo biocompatibility and biostability of modified polyurethanes," *J. Biomed. Mater. Res.*, 36:246-257,1997.

Matthews et al., "Electrospinning of collagen nanofibers," *Biomacromolecules*, 3:232-238, 2002.

Megelski et al., "Micro- and nanostructured morphology on electrospun polymer fibers," *Macromolecules*, 35:8456-8466, 2002.

Meo and Rossi, "Predictiion of Young's modulus of single wall carbon nanotubes by molecular-mechanics based on finite element modelling," *Comp. Sci. Tech.*, 66:1597-1605, 2006.

Meyers et al., "Biological materials: structure and mechanical properties," *Prog. Materials Sci.*, 53:1-206, 2008.

Murray and Macnicol, "10-16 year results of Leeds-Keio anterior cruciate ligament reconstruction," *The Knee*, 11:9-14, 2004.

Noyes et al., "Biomechanical analysis of human ligament grafts used in knee-ligament repairs and reconstructions," *J. Bone Joint Surg. Am.*, 66:344-352, 1984.

Noyes et al., "Biomechanics of anterior cruciate ligament failure: an analysis of strain-rate sensitivity and mechanisms of failure in primates," *J. Bone Joint Surg. Am.*, 56:236-253, 1974.

Pedicini and Farris, "Mechanical behavior of electrospun polyurethane," *Polymer*, 44:6857-6862, 2003.

Provenzano and Vanderby Jr., "Collagen fibril morphology and organization: implications for force trasmission in ligament and tendon," *Matrix Biology*, 25:71-84, 2006.

Qian and Dickey, "Load transfer and deformation mechanisms in carbon nanotube-polystyrene composites," *Appl. Phys. Lett.*, 76:2868-2870, 2000.

Quintero and Mann, "Rapid production of ultralong amorphous ceramic nanofibers by laser spinning," *Appl. Phys. Lett.*, 90:153109, 2007.

Ramdhanie et al., "Thermal and mechanical characterization of electrospun blends of poly(lactic acid) and poly(glycolic acid)," *Polym. J.*, 38:1137-1145, 2006.

Rasheed et al., "The efficiency of the oxidation of carbon nanofibers with various oxidizing agents," *Carbon*, 45:1072-1080, 2007.

Raspanti et al., "The 3D structure of crimps in the rat Achilles tendon," *Matrix Biology*, 24:503-507, 2005.

Rouse, "Polymer-assisted dispersion of single-walled carbon nanotubes in alcohols and applicability toward carbon nanotube/sol—gel composite formation," *Langmuir*, 21:1055-1061, 2005.

Salvetat et al., "Mechanical properties of carbon nanotubes," *Appl. Phys.*, 69:255-260, 1999.

Salvetat-Delmotte and Rubio, "Mechanical properties of carbon nanotubes: a fiber digest for beginners," *Carbon*, 40:1729-1734, 2002.

Sen et al., "Preparation of single-walled carbon nanotube reinforced polystyrene and polyurethane nanofibers and membranes by electrospinning," *Nano Lett.*, 4:459-464, 2004.

Silver et al., "Viscoelastic properties of self-assembled type I collagen fibers: molecular basis of elastic and viscous behaviors," *Connect. Tissue Res.*, 43:569-580, 2002.

Stankus et al., "Fabrication of biodegradable elastomeric scaffolds with sub-micron morphologies," *J. Biomed. Mater. Res.*, 70:603-614, 2004.

Tan and Resasco, "Dispersion of single-walled carbon nanotubes of narrow diameter distribution," *J. Phys. Chem. B*, 109:14454-14460, 2005.

Tanzi et al., "Chemical stability of polyether urethanes versus polycarbonate urethanes," *J. Biomed. Mater. Res.*, 36:550-559, 1997.

Teo et al., "Electrospun scaffold tailored for tissue-specific extracellular matrix," *Biotechnol. J.*, 1:918-929, 2006.

West and Harner, "Graft selection in anterior cruciate ligament reconstruction," *J. Am. Acad. Orthop. Surg.*, 13:197-207, 2005.

Wnek et al., "Electrospinning of nanofiber fibrinogen structures," *Nano Lett.*, 3:213-216, 2003.

Yeo and Friend, "Electrospinning carbon nanotube polymer composite nanofibers," *J. Exp. Nansci.*, 1:177-209, 2006.

Yoshimoto et al., "A biodegradable nanofiber scaffold by electrospinning and its potential for bone tissue engineering," *Biomaterials*, 24:2077-2082, 2003.

Zhong et al., "An aligned nanofibrous collagen scaffold by electrospinning and its effects on in vitro fibroblast culture," *J. Biomed. Mater. Res.*, 79:456-463, 2006.

\* cited by examiner

ARTIFICIAL LIGAMENTS AND TENDONS COMPRISING MULTIFILAMENTS AND NANOFIBERS AND METHODS FOR MAKING

RELATED APPLICATIONS

This application claims the benefit of U.S. Provisional Patent Application No. 61/046,739, filed Apr. 21, 2008, which is incorporated by reference in its entirety.

BACKGROUND OF THE INVENTION

1. Field of the Invention

The present invention relates generally to nanotechnology and, more particularly, the development and use of artificial (prosthetic) ligaments or tendons comprising nanofibers.

2. Description of Related Art

Ligaments and tendons are bands or sheets of fibrous connective tissue that provide support and stability to the musculoskeletal system. Ligaments extend between adjacent bone structures and serve a primary function of providing appropriate stability to the bone structures to maintain them in an aligned, spaced relation, particularly when subjected to loads in tension or upon torsional movement. Tendons, also capable of withstanding tension, are tough bands of fibrous connective tissue that usually connect muscle to bone.

Over 800,000 injuries to ligaments, tendons and the joint capsule occur every year in the U.S. (Doroski et al., 2007). Among the most common injuries are to the patellar tendon, the anterior cruciate ligament, the posterior cruciate ligament, the medial collateral ligament, the Achilles tendon, the anterior talofibular ligament, the calcaneofibular, the rotator cuff tendons, the acromioclavicular ligament and the gluteus medius tendon (Doroski et al., 2007). Unfortunately, insufficient vascularization impedes complete healing after extreme tearing or rupture of these tissues (Doroski et al., 2007; Freeman et al., 2007; West and Harner, 2005). Therefore, surgical intervention is commonly required to perform autografts, allografts or to treat the injury with prosthetic ligaments or tendons (Freeman et al., 2007; West and Harner, 2005; Jeon et al., 2007; Fujii et al., 1997; Fujishiro et al., 2003; Ciccone et al., 2006; Noyes et al., 1984).

The use of autografts often imparts additional injury to the patient, causing donor site morbidity and increased recovery times, while allograft availability is limited and possesses the risk of transmitting infections and obtaining adverse immunological reactions from the patient (Freeman et al., 2007; West and Harner, 2005). In contrast, artificial ligaments and tendons used in reconstructive surgery do not present these problems but frequently fail over time (Amis and Kempson, 1999; Jadeja et al., 2007). As a consequence, there is a need to develop materials that will allow regeneration or replacement of ligaments and tendons. Such a challenging task should result in biocompatible materials with mechanical properties that will resemble the natural tissues.

SUMMARY OF THE INVENTION

The present invention generally involves the production of ligament- or tendon-mimicking nanofibers ("LTM nanofibers") that may be used as artificial (prosthetic) ligaments or tendons. In particular embodiments, the present invention involves the production and use of LTM nanofibers that optionally comprise carbon nanoparticles, such as carbon nanotubes (CNTs), carbon nanofibers (CNFs), graphene, graphene oxide, and/or other graphene derivatives. The LTM nanofibers of the present invention may be designed to exhibit secondary structural features that offer improved biocompatibility and mechanical characteristics over nanofibers and other materials that lack such secondary structure features.

As used herein, a "ligament- or tendon-mimicking nanofiber" ("LTM nanofiber") is a polymer nanofiber. As used herein, unless specifically limited, "nanofiber" includes fibers having a diameter on the order of nanometers (e.g., up to micrometers), such as, for example, 10 nm, 100 nm, 500 nm, 1000 nm (1 µm), 2000 nm (2 µm), 3000 nm (3 µm), or larger. In some embodiments, the diameter of nanofibers can be specifically limited to less than any of about 10 nm, 100 nm, 500 nm, 1000 nm (1 µm), 2000 nm (2 µm), 3000 nm (3 µm). A non-limiting example of a class of LTM nanofibers is polyurethanes (that is, a polyurethane nanofiber). Non-limiting examples of polyurethanes include Lycra®, Hydrothane™, Elasthane™ and Biospan®. Other examples of classes of polymer nanofibers include poly(ether urethanes), poly (ester urethanes), poly(carbonate urethanes), silicone containing poly(ether urethanes), silicone containing poly(ester urethanes), silicone containing poly (carbonate urethanes), polyureas (and derivatives), and blends thereof. Another example of a class of ligament- or tendon-mimicking nanofibers is a polyamide nanofiber (e.g., a nylon nanofiber). Chemically modified derivatives of members of the classes discussed herein are also contemplated. Collagen nanofibers and elastin nanofibers are also contemplated as ligament- or tendon-mimicking nanofibers. Blends of all of these exemplary ligament- or tendon-mimicking nanofibers are also contemplated. In certain embodiments, an LTM nanofiber exhibits one or more properties selected from the group consisting of: (a) a Young modulus of about 0.1-3000 MPa; (b) a tensile strength value of about 10-100 MPa; (c) a cross-sectional area of about 1-150 mm$^2$; (d) a stiffness of about 50-1000 N/mm; and (e) an ultimate tensile load of about 1000-6000 N. In certain embodiments, an LTM nanofiber is further defined as a biocompatible LTM nanofiber.

One general aspect of the present invention contemplates a LTM nanofiber exhibiting one or more properties selected from the group consisting of: (a) a Young modulus of about 0.1-3000 MPa; (b) a tensile strength value of about 10-100 MPa; (c) a cross-sectional area of about 1-150 mm$^2$; (d) a stiffness of about 50-1000 N/mm; and (e) an ultimate tensile load of about 1000-6000 N. The LTM nanofiber may comprise any polymer discussed herein. For example, the LTM nanofiber may comprise a polymer selected from the group consisting of Lycra®, Hydrothane™, Elasthane™ and Biospan®. An LTM nanofiber may further comprise a carbon nanoparticle, as that term is defined herein. The carbon nanoparticle may be chemically functionalized. The carbon nanoparticle may be further defined as a carbon nanofiber (CNF). The CNF may be chemically functionalized. For example, the CNF may be oxidized to form an oxidized CNF. The carbon nanoparticle may be further defined as a carbon nanotube (CNT). The CNT may be a single-walled CNT (SWNT) or a multiwalled CNT (MWNT).

In certain embodiments, an LTM exhibits two of properties (a)-(e), as defined above. In certain embodiments, an LTM exhibits three of properties (a)-(e), as defined above. In certain embodiments, an LTM exhibits four of properties (a)-(e), as defined above. In certain embodiments, an LTM exhibits all five of properties (a)-(e), as defined above.

LTM nanofibers of the present invention may be biocompatible.

The present invention also contemplates multifilaments, such as multifilaments comprising two or more LTM nanofibers. In certain embodiments, the multifilament exhibits a secondary structure, as that term is defined herein. The LTM nanofibers of a multifilament may comprise any polymer as discussed herein. In certain embodiments, the LTM nanofiber comprises a polymer selected from the group consisting of Lycra®, Hydrothane™, Elasthane™ and Biospan®.

Multifilaments may also comprise carbon nanoparticles. For example, one or more LTM nanofibers of a multifilament may further comprise a carbon nanoparticle. The carbon nanoparticle may be of any type described herein, such as an chemically functionalized carbon nanoparticle (e.g., an oxidized CNF), a CNF, or a CNT (e.g., a SWNT or a MWNT). Such as described above, the LTM nanofibers comprised within a multifilament may exhibit two of properties (a)-(e) as described above. The LTM nanofibers comprised within a multifilament may exhibit three, four, or all five of properties (a)-(e) as described above. The multifilament may be biocompatible.

Methods of making LTM nanofibers of the present invention are also contemplated. For example, methods comprising electrospinning a polymer to form a nanofiber are contemplated. The polymer may be any polymer discussed herein, such as a polymer is selected from the group consisting of Lycra®, Hydrothane™, Elasthane™ and Biospan®. The method may further comprise incorporating a carbon nanoparticle into the ligament- or tendon-mimicking nanofiber. The carbon nanoparticle may be any carbon nanoparticle discussed herein (e.g., an oxidized CNF), a CNF, or a CNT (e.g., a SWNT or a MWNT). In certain embodiments, the carbon nanoparticle is dispersed in the polymer prior to formation of the LTM nanofiber. Such as discussed above, in methods of making LTM nanofibers, the LTM nanofiber may exhibit two of properties (a)-(e) as they are defined above. The LTM nanofibers that are made via methods of the present invention may exhibit three, four, or all five of properties (a)-(e) as described above. The LTM nanofibers made via methods of the present invention may be biocompatible. In certain embodiments, more than one LTM nanofiber is made. Such methods may further comprise, for example, assembling the LTM nanofibers into a multifilament. The multifilament so assembled may exhibit a secondary structure, and may be biocompatible.

Also contemplated by the present invention is a method of altering a mechanical property of a first nanofiber, comprising incorporating a carbon nanoparticle into the first nanofiber to produce a second nanofiber, where the second nanofiber is an LTM. The first and second nanofibers may comprise any polymer as described herein. For example, each nanofiber may comprise a polymer selected from the group consisting of Lycra®, Hydrothane™, Elasthane™ and Biospan®. Mechanical properties may include any mechanical property of a nanofiber as known to those of skill in the art, including, but not limited to, Young modulus, flexural modulus, stiffness, tensile strength and ultimate tensile load.

Another general aspect of the present invention contemplates a method of promoting the growth of a fibroblast on a multifilament comprising contacting the multifilament with the fibroblast, where the multifilament comprises two or more LTM nanofibers. The multifilament may exhibit a secondary structure. The LTM nanofibers may comprise any polymer discussed herein, such as a polymer selected from the group consisting of Lycra®, Hydrothane™, Elasthane™ and Biospan®. The method may take place in vitro or in vivo. The LTM nanofibers comprised within a multifilament may exhibit three, four, or all five of properties (a)-(e) as described above. The multifilament may be biocompatible.

Artificial ligaments and tendons are also contemplated by the present invention. For example, the present invention, in certain embodiments, regards an implanted artificial ligament comprising a multifilament, where the multifilament comprises two or more LTM nanofibers, where the artificial ligament is operably connected between two bones. The multifilament may exhibit a secondary structure. Each of the nanofibers comprised within the multifilament may comprise any polymer as described herein. For example, each of the nanofibers may comprise a polymer selected from the group consisting of Lycra®, Hydrothane™, Elasthane™ and Biospan®. The LTM nanofibers comprised within a multifilament may exhibit three, four, or all five of properties (a)-(e) as described above. The multifilament may be biocompatible.

Also contemplated by the present invention is an artificial tendon comprising a multifilament, where the multifilament comprises two or more LTM nanofibers, where the artificial tendon is operably connected between a bone and a muscle. The multifilament may exhibit a secondary structure. Each of the nanofibers comprised within the multifilament may comprise any polymer as described herein. For example, each of the nanofibers may comprise a polymer selected from the group consisting of Lycra®, Hydrothane™, Elasthane™ and Biospan®. The LTM nanofibers comprised within a multifilament may exhibit three, four, or all five of properties (a)-(e) as described above. The multifilament may be biocompatible.

Some embodiments of the present prosthetic ligaments or tendons comprise: a sterile, biocompatible multifilament comprising a plurality of ligament- or tendon-mimicking (LTM) nanofibers having a secondary structure, the multifilament exhibiting one or more properties selected from the group consisting of: (a) a Young modulus of about 0.1-3000 MPa; (b) a tensile strength value of about 10-100 MPa; (c) a cross-sectional area of about 1-150 $mm^2$; (d) a stiffness of about 50-1000 N/mm; and (e) an ultimate tensile load of about 1000-6000 N. In some embodiments, the multifilament exhibits a Young modulus less than about 500 MPa. In some embodiments, the multifilament exhibits a Young modulus less than about 20 Mpa. In some embodiments, the multifilament exhibits a tensile strength between about 39 MPa and about 60 MPa.

In some embodiments of the present prosthetic ligaments or tendons, the secondary structure comprises one or more crimping angles in each of at least a portion of the plurality of LTM nanofibers. In some embodiments, at least a portion of the crimping angles are between about 3 degrees and about 25 degrees. In some embodiments, the at least a portion of the crimping angles are between about 6 degrees and about 17 degrees. In some embodiments, the at least a portion of the crimping angles are between about 6 degrees and about 10 degrees. In some embodiments, the at least a portion of the crimping angles are between about 13 and about 17 degrees.

In some embodiments of the present prosthetic ligaments or tendons, the multifilament comprises a helically wound tubular structure, and where the secondary structure comprises a plurality of overlapping nanofiber crossings each having a crossing angle. In some embodiments, the crossing angles of at least a portion of the nanofiber crossings are between about 3 degrees and about 25 degrees. In some embodiments, the crossing angles of at least a portion of the nanofiber crossings are between about 6 degrees and about 17 degrees.

In some embodiments of the present prosthetic ligaments or tendons, the LTM nanofibers comprise a polymer selected from the group consisting of Lycra®, Hydrothane™, Elasthane™ and Biospan®. In some embodiments, each of at least a portion of the plurality of LTM nanofibers further comprises a carbon nanoparticle. In some embodiments, the carbon nanoparticle is further defined as a chemically functionalized carbon nanoparticle. In some embodiments, the carbon nanoparticle is further defined as a carbon nanofiber (CNF). In some embodiments, the CNF is a chemically functionalized CNF, further defined as an oxidized CNF. In some embodiments, the carbon nanoparticle is further defined as a carbon nanotube (CNT).

Some of the present methods of making prosthetic ligament or tendon, comprise: electrospinning a biocompatible polymer to form a plurality of ligament- or tendon-mimicking (LTM) nanofibers; and grouping the plurality of nanofibers into a multifilament having a secondary structure and exhibiting one or more properties selected from the group consisting of: (a) a Young modulus of about 0.1-3000 MPa; (b) a tensile strength value of about 10-100 MPa; (c) a cross-sectional area of about 1-150 mm$^2$; (d) a stiffness of about 50-1000 N/mm; and (e) an ultimate tensile load of about 1000-6000 N. In some embodiments, the electrospinning and at least a portion of the grouping are simultaneous. In some embodiments, the multifilament exhibits a Young modulus less than about 500 MPa. In some embodiments, the multifilament exhibits a Young modulus less than about 20 Mpa. In some embodiments, the multifilament exhibits a tensile strength between about 39 MPa and about 60 MPa.

In some embodiments of the present methods, the polymer is selected from the group consisting of Lycra®, Hydrothane™, Elasthane™ and Biospan®. In some embodiments, the method further comprises incorporating a carbon nanoparticle into the ligament- or tendon-mimicking nanofiber. In some embodiments, the carbon nanoparticle is dispersed in the polymer prior to electrospinning. In some embodiments, the carbon nanoparticle is further defined as a chemically functionalized carbon nanoparticle. In some embodiments, the carbon nanoparticle is further defined as a carbon nanofiber (CNF). In some embodiments, the CNF is a chemically functionalized CNF, further defined as an oxidized CNF. In some embodiments, the carbon nanoparticle is further defined as a carbon nanotube (CNT).

Some embodiments of the present method of promoting the growth of a fibroblast on a prosthetic ligament or tendon, comprise: positioning a prosthetic ligament or tendon in contact with a fibroblast, the prosthetic ligament or tendon comprising a biocompatible multifilament comprising a plurality of ligament- or tendon-mimicking (LTM) nanofibers having a secondary structure, the multifilament exhibiting one or more properties selected from the group consisting of: (a) a Young modulus of about 0.1-3000 MPa; (b) a tensile strength value of about 10-100 MPa; (c) a cross-sectional area of about 1-150 mm$^2$; (d) a stiffness of about 50-1000 N/mm; and (e) an ultimate tensile load of about 1000-6000 N. In some embodiments, the LTM nanofibers comprise a polymer selected from the group consisting of Lycra®, Hydrothane™, Elasthane™ and Biospan®. In some embodiments, the positioning is done in vitro. In some embodiments, the positioning is done in vivo.

"Contacting" or "positioning in contact with," when applied to a cell, is used herein to describe the process by which a composition of the invention (for example, an LTM nanofiber) is placed in direct juxtaposition with the target cell.

As used herein, "operably connected" refers to a coupling of components (e.g., LTM nanofibers) together to enable the components to provide a desired operation or movement. For example, LTM nanofibers may be operably connected in between two bones such that the LTM nanofibers function as an artificial ligament. As another example, LTM nanofibers may be operably connected in between a bone and a muscle, such that the LTM nanofibers function as an artificial tendon.

The terms "a" and "an" are defined as one or more unless this disclosure explicitly requires otherwise.

The use of the term "or" in the claims is used to mean "and/or" unless explicitly indicated to refer to alternatives only or the alternatives are mutually exclusive, although the disclosure supports a definition that refers to only alternatives and "and/or"

The term "about," refers to ranges within 10%, such as within 5%, within 1%, or within 0.5% of what is specified.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has," or "includes" one or more steps is not limited to possessing only those one or more steps and also covers other unlisted steps.

The term "effective," as used herein, means adequate to accomplish a desired, expected, or intended result.

Other features and associated advantages will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The invention may be better understood by reference to one of these drawings in combination with the detailed description of specific embodiments presented herein.

DETAILED DESCRIPTION OF EMBODIMENTS

Figure 1:
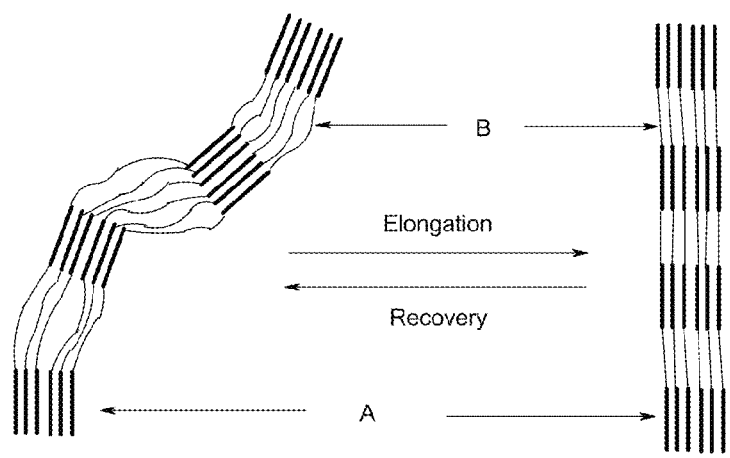
FIG. 1. Morphological model of polyurethanes. (A) hard segments; (B) soft segments (Boretos, 1980; Gogolewski, 1989).

The present invention is based on the discovery that certain synthetic polymers can be formed into nanofibers and assembled into specific structures that may possess mechanical properties similar to natural ligaments and tendons. As discussed herein, these polymers may be formed into nanofibers having particular secondary structural features that mimic structural features of natural ligaments and tendons, allowing for production of novel artificial ligaments and tendons.

I. Polymers of the Present Invention

Many polymers, both natural and synthetic, may be formed into nanofibers. To create artificial ligaments or tendons, certain polymers are more preferable to use than others. In certain embodiments, those polymers having properties similar to those of natural ligaments and tendons may be in the present invention, as discussed below.

Several polymers, such as poly L-lactic acid (Freeman et al., 2007), poly(D,L-lactic acid-co-glycolic acid) (Baashur et al., 2006), collagen (Zhong et al., 2006) and poly(ether urethane) ureas (Stankus et al., 2004) have been prepared as potential scaffolds for ligaments and tendons. However, these materials are designed as scaffolds that can biodegrade before promoting full tissue regeneration. More-permanent prosthetic ligaments and tendons have been prepared from non-biodegradable synthetic materials; among the most common polymers for this purpose may include poly(ethylene terephthalate) or PET (Leeds-Keio®, LARS®, Proflex®, Lygeron®, ABC Surgicraft®, Ligastic®, SEM® and Stryker®), polypropylene or PP (Kennedy Ligament Augmentation Device®), ultrahigh molecular weight polyethylene or UHMWPE (Raschel® and Braided PHP®) and poly-tetrafluoroethylene or PTFE (Gore-Tex®)(Amis and Kempson, 1999; Jadeja et al., 2007; Laurencin and Freeman, 2005; Guidoin et al., 2000; Lavoie et al., 2000).

Although these synthetic materials have been used since 1983 in different assemblies (woven tubes, braids and yarns) (Guidoin et al., 2000), their secondary structures do not present any crimping angles like collagen in ligaments and tendons, which allows small strains at low stresses. Furthermore, even though the tensile strengths in the natural tissues and the industrial polymers used in prostheses are similar, the Young moduli are quite different, so the materials are quite "stiff" and do not have elasticity (see Tables 1 and 2).

TABLE 1

Mechanical properties of polymers used for ligament and tendon prostheses (Brandrup and Immergut, 1985).

| | Young modulus (MPa) | Tensile strength (MPa) |
|---|---|---|
| PP | 1032-1720 | 29-39 |
| PET | 2700-4000 | 47-70 |
| UHMWPE | 2400 | 37-47 |
| PTFE | 500 | 25-38 |

TABLE 2

Mechanical properties of natural tissues (West and Harner, 2005).

| | Young modulus (MPa)* | Tensile strength (MPa)* | Cross sectional area (mm$^2$) |
|---|---|---|---|
| Anterior cruciate ligament | 5.5 | 49 | 44 |
| Patellar tendon | 18 | 85 | 35 |
| Quadruple hamstring | 15 | 77 | 53 |
| Quadriceps tendon | 7.5 | 38 | 62 |

*Estimated from stiffness values (N/mm) and ultimate tensile loads (N).

Nanofibers of the present invention typically may withstand high tensile strengths (will not break easily) while also being elastic enough to allow flexibility, so extension and contraction of the nanofiber can emulate natural ligaments and tendons. Several studies have reported and proposed failure mechanisms for ligament and tendon prostheses (Amis and Kempson, 1999; Guidoin et al., 2000; Lavoie et al., 2000; Murray and Macnicol, 2004; Margevicius et al., 1996), but no investigations seem to address that one of the causes might be the difference in these mechanical properties and the lack of resemblance in the secondary structure. Thus, in general, particular polymers of the present invention will possess moduli and other properties similar to natural ligaments or tendons, as such properties suggest that the materials are more flexible than those currently used and should better resemble the natural tissues.

Polyurethane elastomers are a non-limiting example of a class of polymers that may be employed by the present invention. Polyurethane elastomers are segmented block copolymers consisting of hard crystalline segments dispersed between flexible amorphous segments. The hard segments are made of aliphatic or aromatic diisocyanates, which promote intermolecular hydrogen bonding and result in the glassy or crystalline phase that imparts toughness to the material (FIG. 1, segment A). The soft segments usually comprise polyethers, polybutadienes, or polyesters which are responsible for the formation of elastomeric domains that provide flexibility and elastic recovery to the polymer (FIG. 1, segment B) (Boretos, 1980; Gogolewski, 1989).

The qualities of the chemical nature and physical properties of these two phases is exemplified by Lycra® garments. When this polymer is stretched, the elastomeric domains uncoil and the material elongates in the stretching direction, while the crystalline phase keeps the molecules from sliding past each other. When the external force is withdrawn, the elastomeric domains go back to their coiled state, and the polymer recovers its original size (FIG. 1) (Boretos, 1980; Gogolewski, 1989). Ligaments and tendons present a similar behavior when subjected to extension and contraction. Therefore, the elasticity and toughness exhibited by polyurethanes make them useful for the applications discussed herein.

Non-limiting examples of polyurethane elastomers that may be employed in the present invention include poly(ether urethanes) such as Lycra®, Hydrothane™, Elasthane™ and Biospan®. These polyurethane elastomers may be used alone or in combination with one another. As shown in Table 3, these elastomers offer mechanical properties that are closer to the properties of natural ligaments and tendons than any of the commercially available materials discussed above. In particular, these polyurethanes and the natural tissues present similar tensile strengths: these similarities suggest that each polyurethane is elastic but strong enough to withstand stresses that mimic the body. Moreover, all of these polymers (except Lycra®) are intended for biomedical uses. Furthermore, Biospan® and Elasthane™ have FDA approval for long-term uses in the body and are presently used in several biomedical devices.

TABLE 3

Mechanical properties of non-limiting examples of polyurethanes suitable for use in embodiments of the present invention

| Polymer | Modulus (MPa) | Tensile strength (MPa) |
|---|---|---|
| Biospan ® | 13 (Initial) | 42.5 |
| Elasthane ™ 80A | 36 (Flexural)* | 44 |

TABLE 3-continued

Mechanical properties of non-limiting examples of polyurethanes suitable for use in embodiments of the present invention

| Polymer | Modulus (MPa) | Tensile strength (MPa) |
|---|---|---|
| Elasthane ™ 55D | 149 (Flexural)* | 54 |
| Elasthane ™ 75D | 1993 (Flexural)* | 60 |
| Hydrothane ™ 75D | Not available | 39-54** |

*Flexural modulus used as an approximation of Young modulus.
**Value depends on hydration state.

The polymer materials may be acquired by various commercial suppliers. For example, Elasthane™ and Biospan® may be obtained from The Polymer Technology Group (acquired by DSM and possibly now known as DSM PTG) (Berkeley, Calif.); Hydrothane™ (hydrophilic and elastic) may be obtained from Cardiotech International (possible now known as Advansource Biomaterials Corporation) (Wilmington, Mass.); and Lycra® may be obtained from Invista (formerly DuPont) (Wichita, Kans.).

II. Methods of Making LTM Nanofibers

At present, the most common method used to make nanofibers is through the use of electrospinning. This method may be employed to prepare LTM nanofibers of the present invention ("electrospun LTM nanofibers" or "ELTM nanofibers"). The first work describing the electrospinning process is credited to Formhals, who obtained several U.S. patents in the 1930's and 1940's to produce cellulose acetate, cellulose propionate and wool-cellulose acetate fibers (U.S. Pat. Nos. 1,975,504; 2,160,962; 2,187,306; 2,323,025; 2,349,950). However, the process was not investigated thoroughly in the subsequent years until the last decade, where electrospinning has become extensively studied because of its simplicity and the potential to produce inorganic and polymeric fibers with micrometer and nanometer size diameters (Li and Xia, 2004). Nanofibers produced by this technique are currently being explored for a variety of applications, such as enzyme and catalyst supports, filtration media, military protective clothing, sensors, electronic and optical devices, and reinforced nanocomposites (Li and Xia, 2004; Huang et al., 2003; Matthews et al., 2002; Wnek et al., 2003; Yoshimoto et al., 2003; Kenawy et al., 2002; MacDiarmid et al., 2001; Ding et al., 2004; Kessick and Tepper, 2006; Dror et al., 2003).

Figure 2:
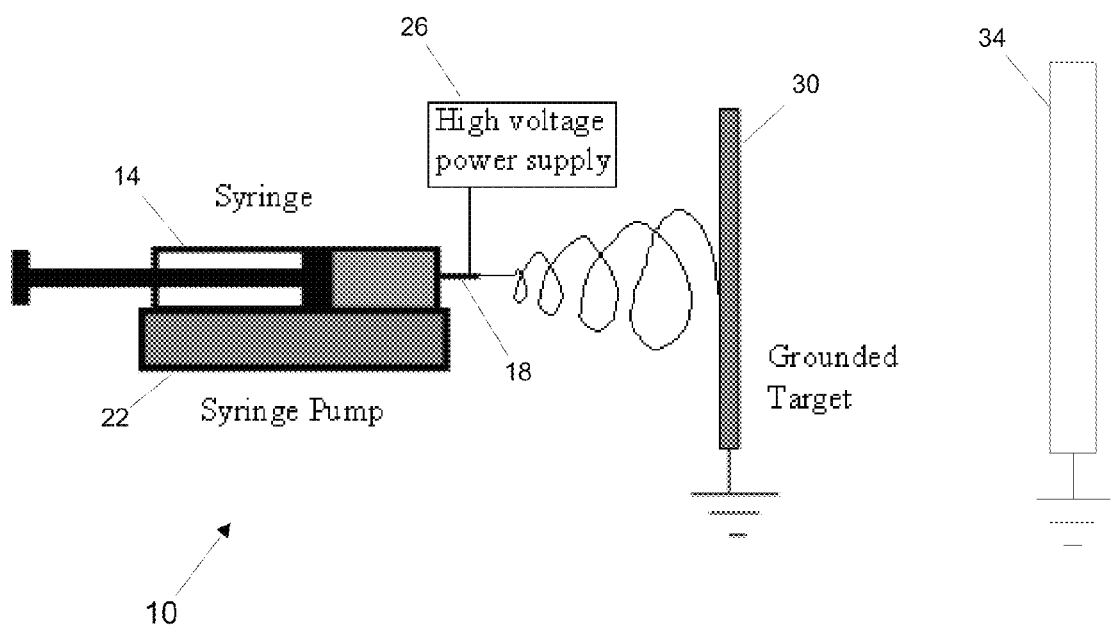
FIG. 2. Electrospinning set-up.

Electrospinning is the process in which a polymer solution is ejected from a reservoir (i.e., syringe) that has a nozzle (i.e., needle or a capillary tube) directly attached to a high power supply (see FIG. 2). This power source generates a high voltage difference, usually selected between about 5-30 kV, which promotes the ejection of a liquid jet followed by solvent evaporation and the formation of a dry polymer fiber, which deposits on a grounded target. In certain embodiments of the present invention, the voltage ranges between about 1 kV and 30 kV (e.g., about 5 kV, 10 kV, or 15 kV).

In the embodiment shown in FIG. 2, the electrospinning apparatus 10 comprises a syringe 14 having a needle 18, a syringe pump 22, a high-voltage power supply 26, and a grounded target 30. Syringe pump 22 is coupled to syringe 14 such that the syringe pump is activatable to actuate the syringe or otherwise cause the polymer to be ejected or pushed out of the syringe, such as, for example, via needle 18. In some embodiments, the apparatus 10 is configured such that the polymer can be pushed out of the syringe at a predetermined flowrate. Needle 18 can be any suitable size, such as, for example between 6 gauge and 34 gauge, e.g., 7, 8, 9, 10, 11, 12, 13, 14, 15, 16, 17, 18, 19, 20, 21, 22, 23, 24, 25, 26, 27, 28, 29, 30, 31, 32, 33, 34, larger than 6 gauge, smaller than 34 gauge, or any range between any of these sizes. In certain embodiments, the distance between the tip of needle 18 and grounded target 26 ranges between about 0.5 cm and 40 cm. For example, the distance may be less than, greater than, between, or equal to any of about: 0.75, 1, 2, 3, 4, 5, 6, 7, 8, 9, 10, 11, 12, 13, 14, 15, 20, 25, or 30 cm.

In the embodiment shown, grounded target 18 is a mandrel having a cylindrical shape with a circular cross section that is continuous along its length (e.g., along the longitudinal axis of the mandrel). In other embodiments, the mandrel can be configured to have any suitable cross-sectional shape, such as, for example, square, triangular, rectangular, fanciful or the like. In some embodiments, the cross-sectional shape can include one or more angles, such as, for example, one or more acute angles, one or more right angles, and/or one or more obtuse angles to create secondary structures (e.g., crimping angles). The mandrel can be configured to rotate clockwise and/or counter-clockwise about a rotational axis such as its longitudinal axis (e.g., can be a rotating mandrel). The mandrel can be configured to rotate eccentrically around a rotational axis. The mandrel can be configured to be moved translationally. For example, the mandrel can be configured to move in an upwardly (e.g., upwards along the longitudinal axis of the mandrel), in a down direction (e.g., downwards along the longitudinal axis of the mandrel), and/or laterally relative to syringe 14 and needle 18 (e.g., side-to-side). In some embodiments, the mandrel (or any other grounded target) can be configured to move in any one or combination of the described ways, such as, for example, intermittently or periodically. For example, the mandrel can be configured such that it can be rotated sequentially clockwise and counter-clockwise in an alternating fashion.

In the embodiment shown, apparatus 10 further comprises a supplemental grounded target 34. Supplemental grounded target 34 can be, for example: a flat plate that lies in a plane perpendicular (or about or substantially perpendicular to needle 18, a mandrel (e.g., rotating or non-rotating), or any other suitable shape. Supplemental grounded target can be configured to mediate or control airflow or other characteristics during the electrospinning process, and/or can be configured and/or used to collect additional nanofibers. In certain embodiments, the distance between grounded target 30 and supplemental grounded target 34 ranges between about 0.5 cm and 40 cm. For example, the distance may be less than, greater than, between, or equal to any of about: 0.75, 1, 2, 3, 4, 5, 6, 7, 8, 9, 10, 11, 12, 13, 14, 15, 20, 25, or 30 cm.

Other methods of making LTM nanofibers are also possible, such as through melt spinning as described in U.S. Pat. No. 6,382,526; Quintero et al. (2007) and centrifuge spinning as described in Dauner, 2006. Each of these references are incorporated herein by reference.

Some polyurethanes present chemical crosslinking which makes them very difficult to dissolve in common organic solvents, while others present physical crosslinking and will dissolve easier in organic solvents under certain conditions. Non-limiting examples of common solvents for polyurethanes include dimethylformamide (DMF) and dimethylacetamide (DMAc) under high shearing conditions.

Although these solvents might dissolve the polymers, their low vapor pressures present a challenge during electrospinning, in particular, since the solvent evaporates. Another common solvent for electrospinning is tetrahydrofuran (THF), which is a very good polar aprotic organic solvent with lower vapor pressure, which results in a boiling point of 56° C. Solution preparations that may be employed in certain embodiments of the present invention, such as methods that involve electrospinning, include the following: pure DMF, DMAc and DMF-THF, DMAc-THF solvent mixtures at different ratios (e.g., 25:75, 50:50 and 75:25). Solvents employed in methods of the present invention may be obtained from commercial sources. For example, THF and DMF may be acquired from Sigma-Aldrich. Polymer concentrations that may be employed in methods of the present invention may range between, for example, about 1% and 25% wt/wt. For example, a polymer concentration may be about 2.5%, 5%, 7.5%. 10%, 15%, 20% or 25%.

III. Secondary Structures in LTM Nanofibers

Figure 3:
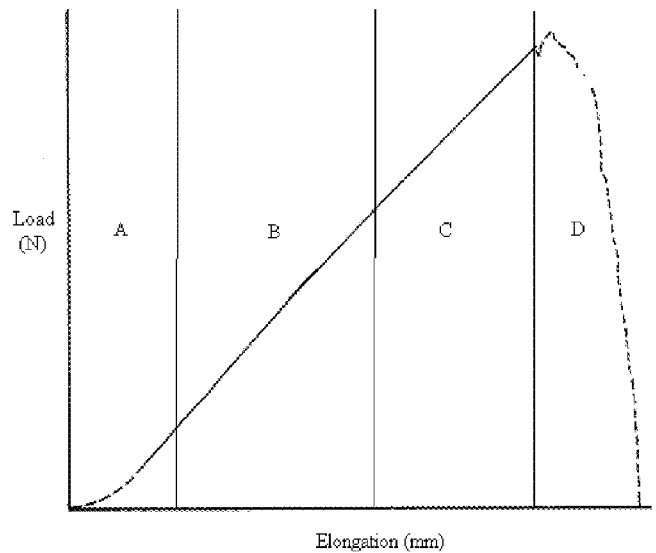
FIG. 3. Load versus elongation curve for ligaments and tendons (Noyes et al., 1984). (A) "toe region", which is associated with the uncrimping of collagen fibers at low stress with a low strain response; (B) a linear region that corresponds to the collagen triple helix stretching, where fibers align and become stiffer; (C) if an excessive stress is applied to the fibers, the crosslinks that keep the collagen triple helix together start breaking up, resulting in deformation and defibrillation; (D) the triple helix yields and fails, resulting in individual fibers slipping past each other, resulting in lack of mechanical strength in the ligaments and tendons (Silver et al., 2002; Noyes et al., 1974).

Collagens are the most abundant proteins in ligaments, tendons, cartilage, bone, cornea and skin. Ligaments and tendons are formed from type I collagen rope-like assemblies with the objective to transmit force between bones or bone and muscle respectively (Provenzano and Vanderby, 2006). FIG. 3 presents the stress (load) vs. strain (elongation) curve for the mechanical behavior of ligaments and tendons. The curve presents the following regions: (A) the "toe region", which is associated with the uncrimping of collagen fibers at low stress with a low strain response; (B) a linear region that corresponds to the collagen triple helix stretching, where fibers align and become stiffer; (C) if an excessive stress is applied to the fibers, the crosslinks that keep the collagen triple helix together start breaking up, resulting in deformation and defibrillation; (D) the triple helix yields and fails, resulting in individual fibers slipping past each other, resulting in lack of mechanical strength in the ligaments and tendons (Silver et al., 2002; Noyes et al., 1974). Embodiments of the present multifilaments and/or prosthetic ligaments or tendons can be configured to have stress-strain curves similar to a portion (up to all) of the stress-strain curve of FIG. 3 (e.g., having a toe region, a linear or substantially linear elastic stretching region, an inelastic deformation region, and/or a failure region).

Although ligaments and tendons are composed mainly of collagen and elastin, the biopolymers are found at different ratios and special angles in these tissues, so different secondary structures are obtained. Secondary structure relates to the architecture of the polymers. As used herein, a 'secondary structure' refers to the alignment of two or more nanofibers, such as LTM nanofibers, in three-dimensional space, where the alignment of each nanofiber is performed in one and two axes at with resulting angles in the overall material from 2-45 degrees. For example, the present invention contemplates a nanofiber composition, such as a multifilament, comprising two or more LTM nanofibers, where the alignment of each nanofiber is performed in one and two axes with resulting angles in the multifilament in ranges of about 5-40 degrees, 10-30 degrees, 2-10 degrees (e.g., 6-8 degrees), or at about 2, 3, 4, 5, 6, 7, 8, 9, 10, 11, 12, 13, 14, 15, 16, 17, 18, 19, 20, 21, 22, 23, 24, 25, 36, 27, 28, 29, 30, 31, 32, 33, 34, 35, 36, 37, 38, 39, 40, 41, 42, 43, 44, or 45 degrees, or any range derivable therein.

Figure 4A:
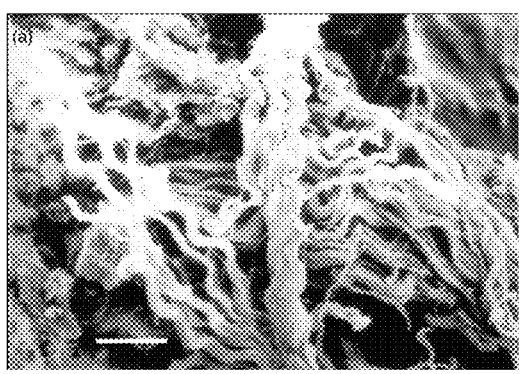
FIGS. 4A and 4B. (A) Scanning Electron Micrograph (SEM) micrograph of human ligaments; (B) SEM micrograph of rat Achilles tendons.
Figure 4B:
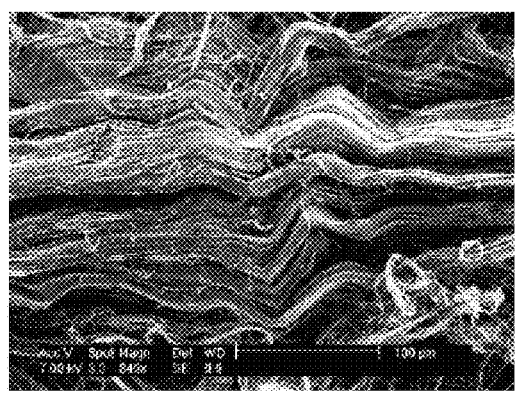
Figure 5:
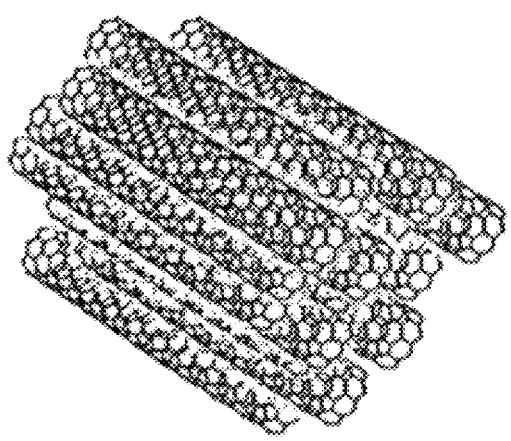
FIG. 5. Carbon nanotubes (CNTs) associated in bundles.

Ligaments present a weaving pattern that is the result of collagen fibers assembled with a 15° angle in human anterior cruciate ligaments (FIG. 4A) (Hukins et al., 1999; Azangwe et al., 2001). In contrast, collagen assembles at a smaller crimping angle of 6-8° in human Achilles tendon along the axis direction (Meyers et al., 2008), as exemplified in rat Achilles tendons (FIG. 5B) (Raspanti et al., 2005). Nevertheless, these natural tissues present analogous mechanical behavior (FIG. 3) but different values of Young modulus, stiffness, tensile strength and ultimate tensile load. Embodiments of the present prosthetic ligaments and tendons (and/or the present LTM nanofibers and/or the present multifilaments comprising such nanofibers) can comprise crimping angles in individual nanofibers similar to the crimping angles depicted in FIGS. 4A and 4B.

Studies suggest that collagen nanofibers' alignment into specific assemblies facilitate fibroblasts growth. Thus, secondary structures may be imparted to nanofibers of the present invention to further mimic the properties of natural ligaments or tendons. A rotating mandrel may be used, for example, for this purpose. Such devices may be obtained from, for example, Custom Design & Fabrication of Virginia Commonwealth University (Richmond, Va.). The rotational and translational movements of the rotating mandrel allows for the arrangement of LTM nanofibers at different angles, thus resulting in an arrangement of nanofibers that mimics the secondary structures of natural ligament and tendons. In other words, a rotating mandrel may be used to impart secondary structure on already-formed nanofibers, such as LTM nanofibers. Various angles may be obtained using this device. Generally speaking, microstructures ranging from "chicken wire" at different angles to mostly parallel nanofibers may be obtained. As produced using a rotating mandrel, aligned scaffolds typically present a higher modulus, higher peak stress and lower percent strain at break (data determined longitudinal to the fiber axes) (Ramdhanie et al., 2006). Methods are known in the literature to study fiber architecture (secondary structure) on cell growth and proliferation. Such methods may be employed to study the LTM nanofibers of the present invention (Doroski et al., 2007; Baashur et al., 2006; Zhong et al., 2006; Lee et al., 2005) (each of which is incorporated herein by reference).

LTM nanofibers of the present invention may be assembled into multifilaments. As used herein, a monofilament is a single, individual filament, such as a single, individual nanofiber (e.g., an LTM nanofiber). A multifilament, as used herein, refers to a nanofiber composition that comprises two or more monofilaments that are not covalently bonded to each other, but are physically associated with one another to form a unitary structure, such as a yarn. As used herein, a "hybrid multifilament" refers to a multicomponent multifilament that comprises one or several multifilament component(s) and one or several monofilament component(s). Hybrid multifilaments comprising two types of LTM nanofibers of the present invention are contemplated.

IV. Incorporation of Carbon Nanoparticles into LTM Nanofibers

LTM nanofibers may, in certain embodiments, incorporate carbon nanotubes (CNTs), carbon nanofibers (CNFs), graphene, graphene oxide, and/or other graphene derivatives. As used herein, "carbon nanoparticles" refers to CNTs and CNFs. For example, carbon nanoparticles may impart different mechanical properties into an LTM nanofiber, as discussed below. Carbon nanoparticles may be imparted into LTM nanofibers using methods known in the literature (Macossay et al., 2006) and as described herein.

A. Carbon Nanotubes and Carbon Nanofibers

CNTs include single walled carbon nanotubes (SWNTs) and multiwalled carbon nanotubes (MWNTs). These compounds and CNFs have different structures and morphologies: while SWNTs are materials made of hollow single rolled up graphene sheets, MWNTs consist of multiple concentric sheets with a hollow core. CNFs, however, include hollow or solid graphene sheets with stacked cones, stacked cups or plates morphologies (Salvetat et al., 1999).

CNTs and CNFs are materials with conjugated C—C $sp^2$ bonds, which results in strong covalent bonds and a remarkable hexagonal network that is capable of distortions for relaxing stress (Salvetat et al., 1999; Salvetat-Delmotte and Rubio, 2002). As a consequence, these carbon allotropes have a unique combination of high strength, flexibility and stiffness, which makes them quite attractive for reinforcing polymer matrices (Qian et al., 2000). Theoretical and experimental studies have indicated that SWNTs have a Young modulus of approximately 1 TPa and tensile strength from 13-53 GPa, while MWNTs possess a Young modulus at 0.9 TPa and tensile strength up to 150 GPa. In contrast, CNFs present more modest mechanical properties with Young modulus varying from 4-6 GPa and tensile strength around 0.2-0.3 GPa (Salvetat et al., 1999; Salvetat-Delmotte and Rubio, 2002; Demczyk et al., 2002; Meo and Rossi, 2006).

Figure 6:
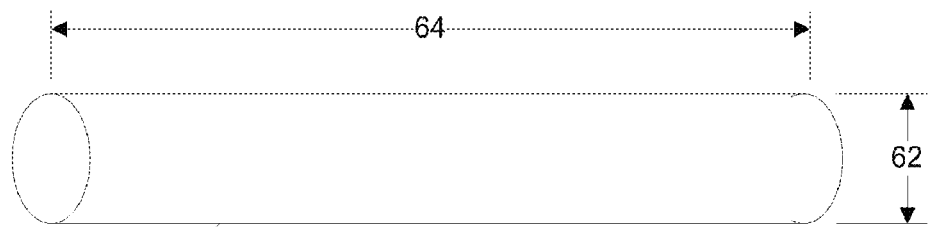
FIG. 6. An individual smooth nanofiber without bends along its length.

However, the same chemical nature ($sp^2$ hexagonal networks) that provides high strength, flexibility and stiffness to CNTs and CNFs is responsible for strong π-π interactions between adjacent graphene sheets: as a consequence, these interactions promote Van der Waals forces that result in CNTs and CNFs aggregating in bundles (FIG. 6). As a result, disentanglement and dispersion of CNTs and CNFs has become one of the most challenging issues to overcome when using these nanomaterials as reinforcing fillers in polymer matrices (Qian et al., 2000). Presently, CNTs may be obtained in small amounts at very high prices, while CNFs present modest properties but are produced in bulk quantities at lower prices. CNFs and CNTs may be obtained from various commercial sources, such as Applied Sciences, Inc. (Cedarville, Ohio) and Nanointegris, Nano-C, mknano, and Cheap Tubes, Inc.

B. Carbon Nanoparticle Dispersions

Several strategies may be used to promote CNTs and CNFs dispersions in LTM nanofibers, such as high speed stirring, sonication, high frequency ultrasound, the use of solvents and detergents, and chemical functionalization (Rouse, 2005; Matarredona et al., 2003; Baskaran et al., 2005; Gong et al., 2000; Tan and Resasco, 2005; Rasheed et al., 2007). As a non-limiting example, dispersion of CNTs and CNFs may be carried out in pure polymer (e.g., polyurethane) solutions using, for example, sonication at room temperature for 5-120 minutes (e.g., 5-60 minutes, 60 minutes, or the like). Weight percentages of carbon nanoparticles dispersed in a polymer may range from 0.1-15%, for example (e.g., 10%).

Chemical functionalization yields functional groups on the CNTs surface that facilitate disruption of the π-π interactions between adjacent nanotubes, thus promoting dispersion. As a consequence, enhanced thermal and mechanical properties of CNTs-polymer composite nanofibers are possible. One non-limiting method of such chemical functionalization is based on the work of Dadmun (Rasheed et al., 2007), where CNFs were oxidized with 6M $HNO_3$, $KMnO_4$, $RuO_4$ and $HNO_3/H_2SO_4$. The product of this reaction, or any other reaction involving oxidation of a CNF, is an "oxidized CNF", as used herein. The ratio of ordered graphitic bands to disordered graphitic sites was determined using Raman spectroscopy and allowed the authors to correlate the reaction conditions to chemical modification. Therefore, one can select different conditions according to the specific conditions and dispersions desired.

Several techniques may be used to assess the stability of the carbon nanoparticles-polymer dispersions. Visual inspection and optical micrographs of the samples offer inexpensive methods to determine dispersions stability, while Raman, Fourier Transform Infrared (FTIR) and UV-VIS spectroscopy allow investigation of the dispersions properties, the disordered/graphitic induced bands ratio on CNTs and CNFs (indicating defect sites), and interactions between nanoparticles and polymers (Rouse, 2005; Matarredona et al., 2003; Baskaran et al., 2005; Gong et al., 2000; Tan and Resasco, 2005; Rasheed et al., 2007). In addition, Scanning Electron Microscopy (SEM) may be used to determine the length and aspect ratio of the CNTs and CNFs before and after dispersion (e.g., after sonication).

V. Characterization of LTM Nanofibers

LTM nanofibers may be characterized via any method known to those of skill in the art. For example, SEM may provide evidence of the nanofiber surface morphology and diameter. Such evidence may be correlated with the method in which the nanofiber was made. Regarding electrospinning methods, for example, studies have demonstrated that low polymer concentrations during electrospinning afford beads or bead-strings (pearl necklace) structures as shown by SEM, while high concentrations are known to increase fiber diameters (Megelski et al., 2002; Lee et al., 2003).

Other characterization methods are available. For example, thermal properties may be investigated using Thermogravimetric Analysis (TGA) or Differential Scanning Calorimetry (DSC). TGA may provide information on the decomposition steps and decomposition temperatures of the materials. To complement this information, DSC may provide information on phase transitions, such as glass transition temperatures (Tg), crystallization and melting temperatures.

Mechanical characterization of the LTM nanofibers may be performed using a tensile tester (e.g., a microtensile tester). This technique provides information such as Young modulus, stiffness, tensile strength and ultimate tensile load.

Regarding the distribution of carbon nanoparticles within the LTM nanofibers, characterization by SEM, TGA, DSC, or tensile (e.g., microtensile) testing may be performed. Additional techniques that may be used to determine properties of carbon nanoparticle-containing LTM nanofibers include Transmission Electron Microscopy (TEM) and Raman spectroscopy. TEM may be used to investigate carbon nanoparticles dispersion and alignment within the polymer nanofibers (Macossay et al., 2006; Li and Xia, 2004; Dror et al., 2003). Raman spectroscopy may provide information on the intermolecular interactions between carbon nanoparticles and the LTM nanofibers.

VI. Biocompatibility

To be used in the body, LTM nanofibers are biocompatible, in certain embodiments. As used herein, the term "biocompatible" refers to any material that does not cause injury or death to the animal or induce an adverse reaction in an animal when implanted into the animal. Adverse reactions include inflammation, infection, fibrotic tissue formation, cell death, and thrombosis. As one example of biocompatible polymers known in the art, biocompatible polyurethanes for short and long term applications have been developed, resulting in the use of these materials as pacemaker leads, vascular grafts, catheters, gastric balloons, and prosthetic valve leaflets (Tanzi et al., 1997; Christenson et al., 2004; Mathur et al., 1997).

One method to examine biocompatibility of the LTM nanofibers of the present invention is to perform cell culture studies. Cells, such as fibroblasts (e.g., NIH 3T3 fibroblasts), may be seeded followed by investigation of cell proliferation, such as at 3, 7 and 14 days of culture. See, e.g., Bashura et al., 2006 (incorporated herein by reference). Cell morphology may then determined, such as through fluorescent images of calcein loaded cells or through hematoxylin and eosin staining. Further, cell number may be obtained by attaching to fluorescently label DNA (Baashur et al., 2006; Lee et al., 2005). In this regard, one may determine if the nanofiber promotes the growth of the cell.

VII. Additional Explanation and Examples

In certain embodiments, nanofibers can be formed with the apparatus of FIG. 1 (with or without supplemental grounded target 34) using the materials and parameters included in Table 4. The polymer solutions are prepared according to appropriate parameters (e.g. concentration) prior to electrospinning. A polymer can be added to a solvent according to a desired concentration and dissolved in the solvent (e.g., by way of sonicating the polymer and solvent until the polymer is dissolved). The dissolved solution can then be placed in a syringe (e.g., syringe 14 of FIG. 2), the syringe mounted to a syringe pump (e.g. syringe pump 22 of FIG. 2), and the syringe pump set to an appropriate flowrate. The tip of the needle can be positioned a suitable distance from a grounded target (e.g., grounded target 30 of FIG. 33), such as, for example, at a distance of 24 cm. A voltage (e.g., 15 KV) can be applied to the needle (e.g., at the middle of the needle), and the syringe pump can be turned on to begin the electrospinning process. The electrospun fibers are attracted to and collected on the grounded target, such as, for example, a piece of aluminum foil (e.g., for a non-woven matt) and/or a rotating mandrel (e.g., for a woven tube).

Crimping angles 72 can be formed with the apparatus of FIG. 2, such as, for example, with a mandrel having a cross-sectional shape that includes one or more angles, by alternating the direction of and/or momentarily stopping the rotation of the mandrel, by translationally moving the mandrel up and/or down and/or side-to-side, by varying the flowrate of the syringe pump, and/or by any other variation or combination of variations. In some embodiments, the degree 76 of at least a portion (up to all) crimping angles are formed at a predetermined or desired degree 76. For example, when the nanofiber is in a relaxed state, at least a portion (up to all) of crimping angles can be between about 1 and about 90 degrees, between about 1 and about 45 degrees, between about 3 degrees and about 25 degrees, between about 6 degrees and about 17 degrees, between about 6 and about 10 degrees, about 8 degrees, between about 13 and about 17 degrees, about 15 degrees, and/or about or between about any other suitable degree(s).

TABLE 4

Non-limiting Examples of parameters for electrospinning nanofibers

|  | Hydrothane 75D | Elasthane 80A | Elasthane 75D | Elasthane 55D | Biospan |
|---|---|---|---|---|---|
| Rate (mL/min) | 0.05 | 0.03 | 0.03 | 0.03 | 0.03 |
| Voltage (kV) | 15 | 15 | 15 | 15 | 15 |
| Distance (cm) | 24 | 24 | 24 | 24 | 24 |
| Solution | DMF/THF 50:50 | DMAc | DMF | DMF | DMAc |
| Needle Gauge | 22 | 22 | 22 | 22 | 22 |
| Concentration (wt/vol) | 20% | 15%, 20% | 7.5% | 7.5% | 10% |

FIG. 6 illustrates an individual nanofiber 60 having a diameter 62 and a length 64. Nanofiber 60 can be formed with the apparatus of FIG. 2 and the methods or processes described in this disclosure, and/or with any other suitable apparatuses and methods. In the embodiment shown, nanofiber 60 does not comprise crimping angles, and instead, has a substantially "smooth" configuration that is free of crimping angles (but does not necessarily have smooth surfaces). The diameter can be in the nanometer to micrometer range, and the length can be in the micrometer to centimeter range. Nanofibers formed with the same apparatus and method (e.g., sequentially at the same time) may not necessarily have the same diameters or lengths.

Figure 7:
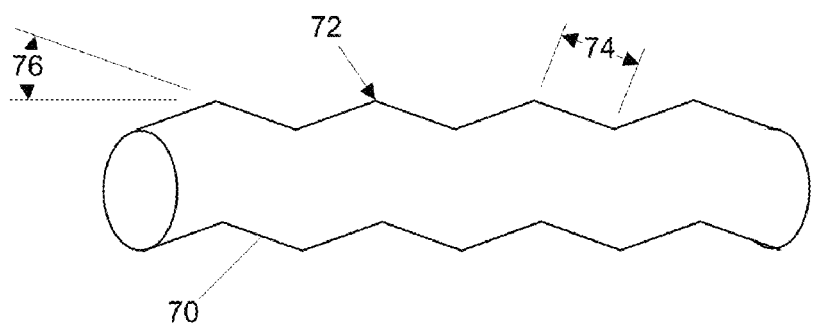
FIG. 7. An individual nanofiber having crimping angles.

FIG. 7 illustrates an individual nanofiber 70 that is similar to nanofiber 60 of FIG. 6, but includes a secondary structure comprising crimping angles 72. Nanofiber 70 can comprise any suitable number of crimping angles, such as, for example, 1, 2, 3, 4, 5, 6, or more. In some embodiments, the number of crimping angles a nanofiber comprises can be expressed in terms of crimping angles per unit length (e.g., 1/nm, 1-5/nm, 1 μm, 1-5 μm, 1/mm, 1-5/mm, 1/cm, 1-5/cm, or the like). Crimping angles need not include a sharp crimp or kink. In some embodiments, crimping angles comprise a soft bend that remains when the nanofiber is in a relaxed state (e.g., when no tensile force is applied to the nanofiber). In some embodiments, crimping angles do comprise a sharp crimp or kink. When a nanofiber 70 includes multiple crimping angles 72, individual crimping angles can be spaced apart from one another by a distance 74. Distance 74 can range from nanometers to micrometers, and need not be equal between all crimping angles. In some embodiments, distances 74 can each be a multiple of the diameter of the nanofiber, such as, for example, 1, 2, 3, 4, 5, 6, 7, 8, 9, 10, 15, 20, 25, 30, 40, 50, 60, 70, 80, 90, or 100 times the diameter of the nanofiber, or any range therein.

Figure 8:
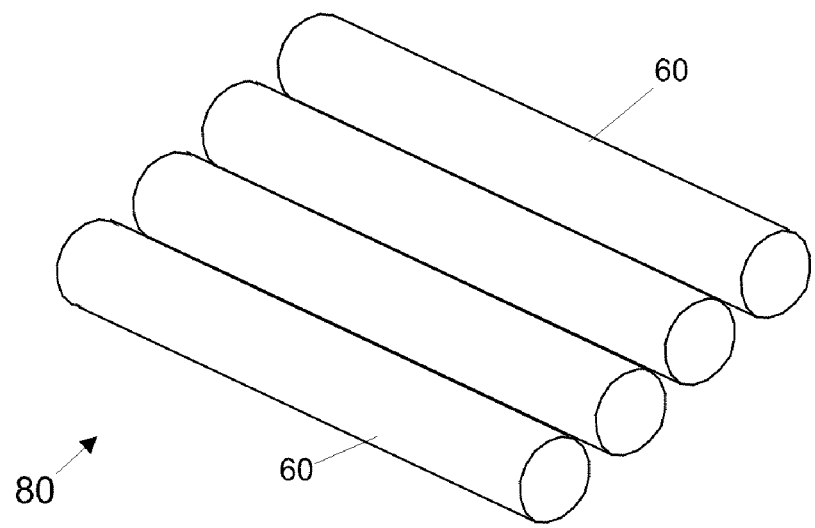
FIG. 8. Multiple individual nanofibers associated into a bundle.

FIG. 8 depicts a plurality of individual nanofibers 60 associated into a multifilament 80. Although multifilament 80 is shown with a flattened cross-sectional configuration, multifilament 80 can comprise any suitable shape, such as, for example, a round cross-sectional shape, or the like. In some embodiments, nanofibers 60 can be interwoven and/or held together with adhesive and/or the like.

Figure 9:
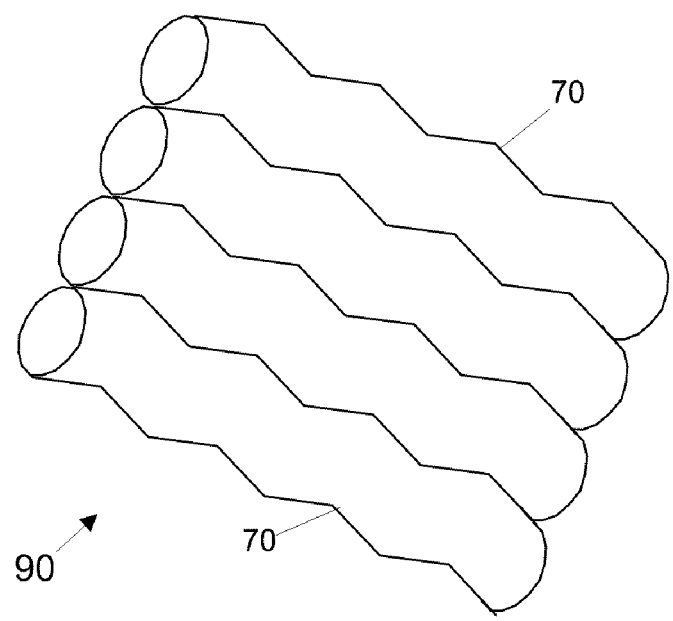
FIG. 9. Individual nanofibers having crimping angles and associated into a bundle.

FIG. 9 depicts a plurality of individual nanofibers 70 associated into a multifilament 90. Although multifilament 90 is shown with a flattened cross-sectional configuration, multifilament 90 can comprise any suitable shape, such as, for example, a round cross-sectional shape, or the like. In some embodiments, nanofibers 70 can be interwoven and/or held together with adhesive and/or the like. Although multifilament 90 is shown having only nanofibers 70 (having crimping angles) and configured such that the crimping angles of adjacent filaments 70 are aligned with one another, other embodiments can have both "smooth" nanofibers 60 and nanofibers 70 (having crimping angles), and/or can have all nanofibers 70 configured such that crimping angles of adjacent nanofibers 70 are not aligned with one another.

Figure 10:
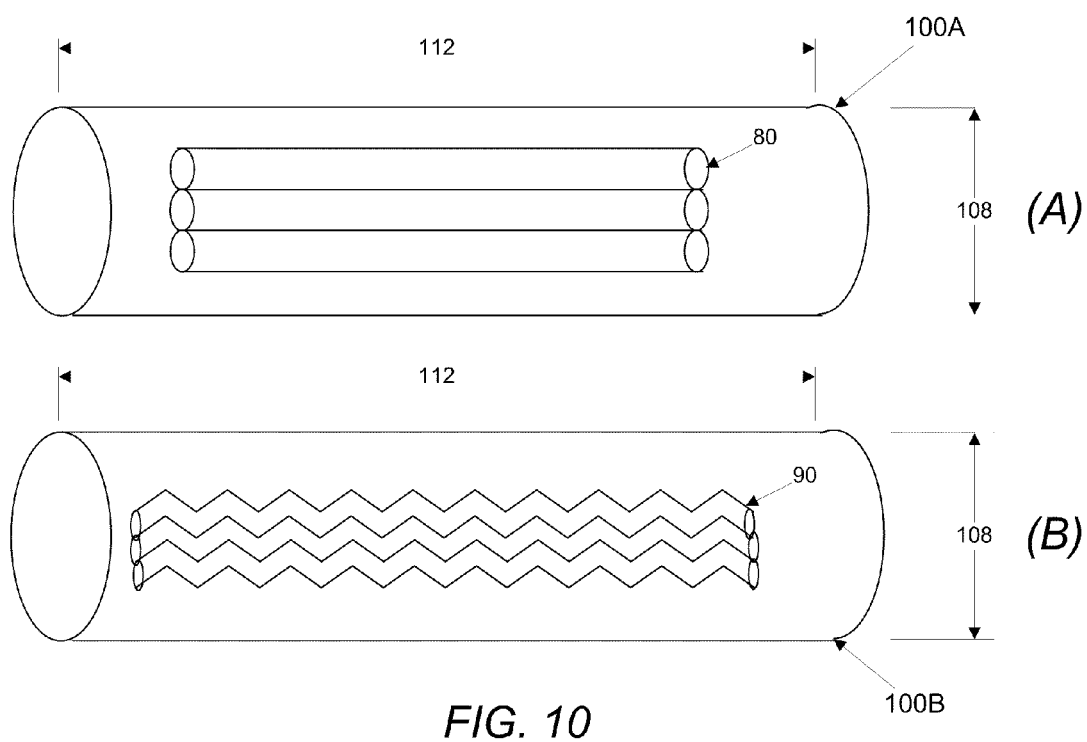
FIG. 10. Prosthetic ligament or tendon including multiple nanofibers.

FIGS. 10A and 10B illustrate two embodiments of prosthetic ligaments or tendons comprising nanofibers. FIG. 10A depicts a prosthetic ligament or tendon 100A comprising a sterile, biocompatible multifilament 80 that comprises a plurality of LTM nanofibers 60. For clarity, only a portion of the nanofibers 60 are shown. The prosthetic ligament or tendon has a diameter 108 and a length 112. In some embodiments, the diameter 108 and/or length 112 correspond to the diameter and/or length of a portion (up to all) of a natural ligament or tendon that the prosthetic is intended to replace. For example, when ligament and/or tendon 100A is intended to replace a human male Achilles tendon, the diameter and/or length can be about equal to an average diameter and/or length of the natural Achilles tendon in male humans. By way of another example, when ligament and/or tendon 100A is intended to replace a human Achilles tendon, the diameter and/or length can be about equal to the diameter and/or length of the natural Achilles tendon in a specific human patient.

FIG. 10B depicts a prosthetic ligament or tendon 100B comprising a sterile, biocompatible multifilament 90 that comprises a plurality of LTM nanofibers 70. For clarity, only a portion of the nanofibers 70 are shown. Prosthetic ligament or tendon 100B is similar to prosthetic ligament or tendon 100A, but the multifilament comprise a plurality of LTM nanofibers having a secondary structure. In the embodiment shown, the secondary structure comprises one or more crimping angles in each of at least a portion (up to all) of the plurality of LTM nanofibers. In other embodiments, the secondary structure can comprise a plurality of overlapping nanofiber crossings, as described in more detail below with reference to FIGS. 11 and 12A-12C. In some embodiments, the secondary structure comprises two secondary structures, such as, for example, crimping angles and overlapping nanofiber crossings.

Figure 11:
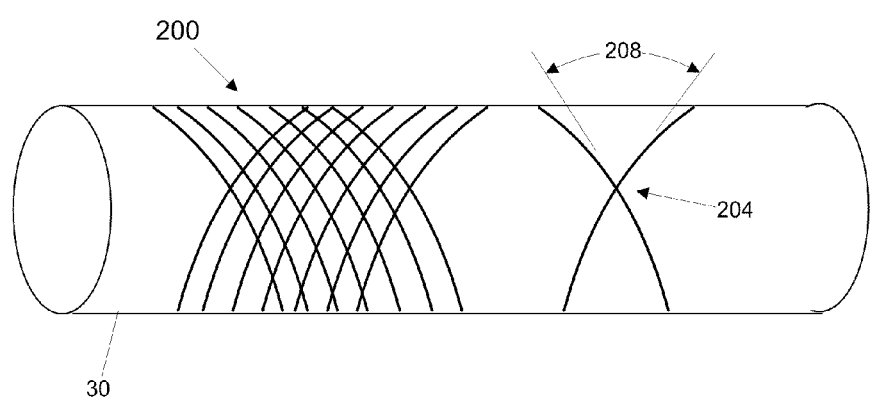
FIG. 11. Tubular prosthetic ligament or tendon comprising nanofibers.

FIG. 11 illustrates the formation of a multifilament 200 about a mandrel 30, the multifilament comprises a plurality of LTM nanofibers 200 (e.g., nanofibers 60, nanofibers 70, or both) having a secondary structure. For clarity, only a portion of the nanofibers 200 are shown. In the embodiment shown, the secondary structure comprises a plurality of overlapping (e.g. wound, woven, interwoven) nanofiber crossings 204 each having a crossing angle 208 such that the multifilament comprises a helically wound tubular structure (e.g., at least when the multifilament is in a relaxed state). In some embodiments, multifilament 200 comprises crossing angles 208 and nanofibers 70 (having crimping angles).

Crossing angles 208 can be formed with the apparatus of FIG. 2, such as, for example, with a rotating mandrel, by translationally moving the mandrel up and/or down, and/or by any other variation or combination of variations. In some embodiments, at least a portion (up to all) of crossing angles are formed at a predetermined or desired degree. For example, when the multifilament is in a relaxed state, at least a portion (up to all) of crimping angles can be between about 1 and about 90 degrees, between about 1 and about 45 degrees, between about 3 degrees and about 25 degrees, between about 6 degrees and about 17 degrees, between about 6 and about 10 degrees, about 8 degrees, between about 13 and about 17 degrees, about 15 degrees, and/or about or between about any other suitable degree(s).

Figure 12A:
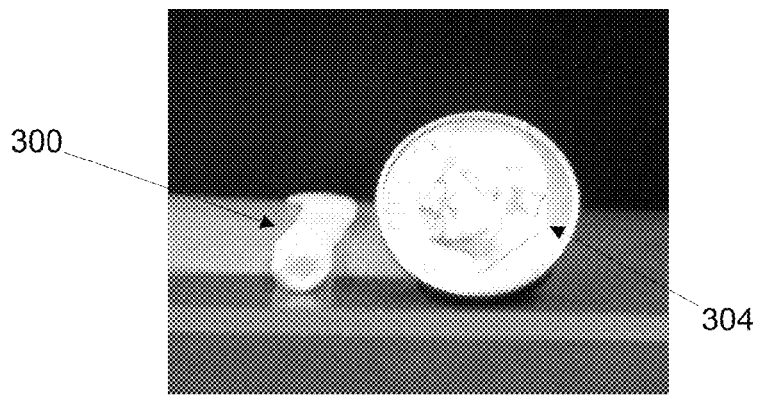
FIG. 12A-12C. Photographs of a tubular (hollow) prosthetic ligament or tendon comprising nanofibers.
Figure 12B:
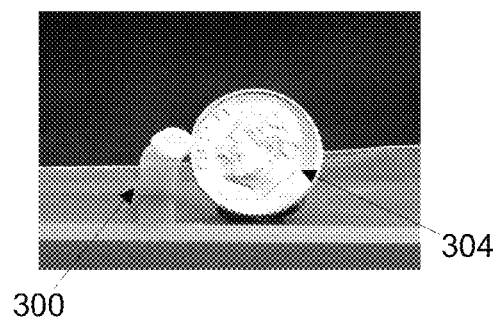
Figure 12C:
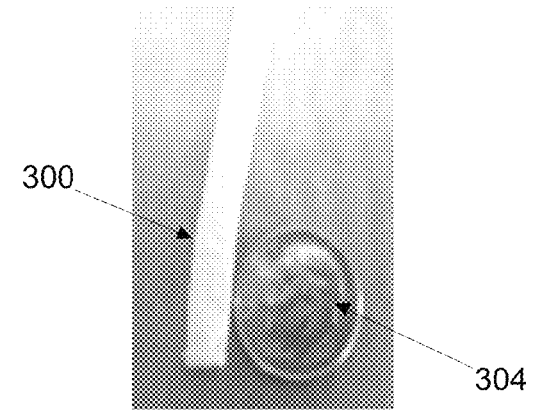

FIGS. 12A-12C depict photographs of one example of a prosthetic ligament or tendon 300 that can be formed with the apparatus of FIG. 2 (with or without supplemental grounded target 34). For reference, prosthetic ligament or tendon is shown with a dime 304. As shown, prosthetic ligament or tendon 304 includes a opening through its center corresponding in size to the diameter of the mandrel (e.g., mandrel 22), around which it was formed. In some embodiments, the mandrel has a diameter of about 1 mm such that the multifilament has a corresponding hollow, tubular structure with an internal diameter of 1 mm or more (e.g., greater than, less than, between, or equal to any of about: 1, 2, 3, 4, 5, 6, 7, 8, or 9 mm, or more). A prosthetic ligament or tendon having a hollow, tubular structure thereby comprises a sidewall having a thickness, such as, for example, of 1 mm or more (e.g., greater than, less than, between, or equal to any of about: 1, 2, 3, 4, 5, 6, 7, 8, or 9 mm, or more).

In this way, prosthetic ligament or tendon 300 is configured to have a stress-strain curve similar to that of a natural ligament or tendon (e.g., FIG. 3). That is, when a tensile force is applied to the prosthetic ligament or tendon, (1) the prosthetic ligament or tendon will initially elongate and the opening will be drawn closed with a relatively lower strain and relatively lower stress (e.g., providing the initial "toe" portion); (2) once the opening is drawn closed, the nanofibers (sidewall) will begin a more-linear elastic region of stress-strain; and (3) eventually the multifilament will fail. In some embodiments, a fourth region will be present in which the multifilament will elongate inelastically (e.g., will be permanently deformed) prior to failure. Similarly, prosthetic ligaments or tendons having multifilaments with crimping angles are also configured to have a stress-strain curve similar to that of a natural ligament or tendon (e.g., with the straightening of the crimping angles providing the initial "toe" portion.

In other embodiments, a multifilament can be solid (e.g., not have a hollow tubular structure). In such embodiments, it will be appreciated that some opening or opening may be present between individual fibers, but such opening will not extend through the entire multifilament and/or will not be larger than the diameters of individual fibers.

Any of the various embodiments of nanofibers, multifilaments, and/or prosthetic ligaments or nanofibers can comprise any of the materials or properties described this disclosure.

VIII. LTM Nanofibers in the Body

As noted herein, artificial (prosthetic) ligaments and tendons are used for the replacement or reconstruction of natural ligaments which have been destroyed or damaged, such as by mechanical injury or disease. When implanting an artificial ligament or tendon, although it is initially fixed in place by some type of fixation device, further fixation after surgery may be achieved by ingrowth of tissue into the ligament or tendon structure. These artificial materials generally require the use of mechanical elements, such as sutures, screws (e.g., metallic interference screws), pins or staples to attach the artificial device to the bone. Such mechanical elements are well-known in the art and may be employed with respect to the present invention. To facilitate the use of mechanical elements, embodiments of the present prosthetic ligaments or tendons can comprise one or more connection elements, members, structures, or the like. For example, embodiments of the prosthetic ligaments or tendons can comprise a first connection member at a first end and a second connection member at a second end. Several examples of mechanical elements and connection elements are described below.

For example, U.S. Pat. No. 6,616,694, incorporated herein by reference, is entitled "Apparatus for Anchoring Autologous or Artificial Tendon Grafts in Bone." The invention describes an anchor assembly for embedding in a bone tunnel which has applications in, for example, repair of the anterior cruciate ligament (ACL) of the knee. It may also be used, for example, for repair of other ligaments such as of the elbow or ankle.

Another type of anchor that may be used in bone tunnels is the Mitek Ligament Anchor available from Mitek Surgical Products, Inc. That anchor includes prongs that lodge into the bone after the anchor has been pulled into position by a suture.

A fixation system for artificial ligaments is described in U.S. Pat. No. 4,955,910, which is incorporated herein by reference. In this system, opposed ends of the artificial ligament are attached to spaced apart bones such that the connections are external of the bones so as to permit a maximum of relative movement between the ligament and the bones while assuring requisite strength in tension. The design enables pretensioning of the ligament, guards against abrasion of the ligament by reason of moving contact with the bones, and is adjustable to accommodate a variety of required sizes.

U.S. Pat. No. 6,764,513 (incorporated herein by reference) describes a crimp tube and knot system to secure an artificial ligament. U.S. Pat. No. 5,356,435 (incorporated herein by reference) describes an element for fixing ligaments to bone, comprising an at least partially hollowed truncated element including an internal conduit adapted to receive one of the end sections of a ligament. A fastening member is provided that extends through the truncated element and clamps the respective end section of the ligament inside the conduit. Connection of an artificial ligament through the use of screws is described in, for example, U.S. Pat. Nos. 4,932,972 and 4,246,660 (each incorporated herein by reference).

A biodegradable sleeve is provided is U.S. Pat. No. 4,584,722 (incorporated herein by reference), which permits attachment of an artificial tendon to a muscle. Sutures that may be used to attach artificial tendons are described in U.S. Pat. No. 3,176,316 (incorporated herein by reference). Suturing methods are also described by Amstutz et al. (1976) (incorporated herein by reference) for attachment of artificial tendons to soft tissue.

All of the methods disclosed and claimed can be made and executed without undue experimentation in light of the present disclosure. While the methods of this invention have been described in terms of embodiments, it will be apparent to those of skill in the art that variations may be applied to the methods and in the steps or in the sequence of steps of the method described herein without departing from the concept, spirit and scope of the invention. All such similar substitutes and modifications apparent to those skilled in the art are deemed to be within the spirit, scope, and concept of the disclosure as defined by the appended claims.

REFERENCES

The following references to the extent that they provide exemplary procedural or other details supplementary to those set forth herein, are specifically incorporated herein by reference.

U.S. Pat. No. 1,975,504
U.S. Pat. No. 2,160,962
U.S. Pat. No. 2,187,306
U.S. Pat. No. 2,323,025
U.S. Pat. No. 2,349,950
U.S. Pat. No. 3,176,316
U.S. Pat. No. 4,246,660
U.S. Pat. No. 4,584,722
U.S. Pat. No. 4,932,972
U.S. Pat. No. 4,955,910
U.S. Pat. No. 5,356,435
U.S. Pat. No. 6,382,526
U.S. Pat. No. 6,616,694
U.S. Pat. No. 6,764,513
Amis and Kempson, *J. Biomed. Mater Res. (Appl Biomater),* 48:534-539, 1999.
Amstutz et al., *J. Biomed. Mater. Res.,* 10:48, 1976.
Azangwe et al., *Clin. Biomechanics,* 16:913-917, 2001.
Baashur et al., *Biomaterials,* 27: 5681-5688, 2006.
Baskaran et al., *Chem. Mater.,* 17:3389-3397, 2005.
Boretos, *Pure & Appl. Chem.,* 52:1851-1855, 1980.
Brandrup and Immergut, In: *Polymer Handbook,* John Wiley and Sons Inc., USA, VI-V87, 1975.
Christenson et al., *J. Biomed. Mater. Res.,* 69A:407-416, 2004.
Ciccone et al., *Am. J. Sports Med.,* 34:24-28, 2006.
Dauner, NanoEurope Conference 2006, 14 Sep. 2006.
Demczyk et al., *Materials Science and Engineering A,* 334: 173-178, 2002.
Ding et al., *Sens. Actuator B,* 101: 373-380, 2004.
Doroski et al., *Biomaterials,* 28:187-202, 2007.
Dror et al., *Langmuir,* 19:7012-7020, 2003.
Freeman et al., *J. Biomech.,* 40: 2029-2036, 2007.
Fujii et al., *The Foot,* 7:139-143, 1997.
Fujishiro et al., *J. Arthroplasty,* 18:524-527, 2003.
Gogolewski, *Colloid Polym. Sci.,* 267: 757-785, 1989.
Gong et al., *Chem. Mater.,* 12:1049-1052, 2000.
Guidoin et al., *Biomaterials,* 21:2461-2474, 2000.
Huang et al., *Comp. Sci. & Tech.,* 63:2223-2253, 2003.
Hukins et al., *J. Mater. Chem.,* 9:629-636, 1999.
Jadeja et al., *The Knee,* 14: 439-442, 2007.
Jeon et al., *Injury,* 38:1247-1253, 2007.
Kenawy et al., *J. Control Release,* 81: 57-64, 2002.
Kessick and Tepper, *Sens. Actuator B,* 117: 205-210, 2006.
Laurencin and Freeman, *Biomaterials,* 26:7530-7536, 2005.
Lavoie et al., *The Knee,* 7:157-163, 2000.
Lee et al., *Biomaterials,* 26:1261-1270, 2005.
Lee et al., *Polymer,* 44:4029-4034, 2003.
Li and Xia, *Adv. Mater.,* 16:1151-1170, 2004.
MacDiamid et al., *Synthetic Metals,* 119:27-30, 2001.
Macossay et al., *Polym. Adv. Technol.,* 17:391-394, 2006.
Margevicius et al., *J. Biomed. Mater. Res.,* 31: 319-328, 1996.
Matarredona et al., *J. Phys. Chem. B,* 107:13357-13367, 2003.
Mathur et al., *J. Biomed. Mater. Res.,* 36:246-257, 1997.
Matthews et al., *Biomacromolecules,* 3:232-238, 2002.
Megelski et al., *Macromolecules,* 35:8456-8466, 2002.
Meo et al., *Comp. Sci. Tech.,* 66:1597-1605, 2006.
Meyers et al., *Prog. Materials Sci.,* 53: 1-206, 2008.
Murray and Macnicol, *The Knee,* 11:9-14, 2004.
Noyes et al., *J. Bone Joint Surg. Am.,* 56:236-253, 1974.
Noyes et al., *J. Bone Joint Surg. Am.,* 66:344-352, 1984.
Provenzano and Vanderby, Jr., *Matrix Biology,* 25:71-84, 2006.
Qian et al., *Appl. Phys. Lett.,* 76:2868-2870, 2000.
Quintero et al., *Appl. Physics Lett.,* 90:153109, 2007.
Ramdhanie et al., *Polym. J.,* 38:1137-1145, 2006.
Rasheed et al., *Carbon,* 45:1072-1080, 2007.
Raspanti et al., *Matrix Biology,* 24:503-507, 2005.
Rouse, *Langmuir,* 21:1055-1061, 2005.
Salvetat et al., *Appl. Phys.,* 69:255-260, 1999.
Salvetat-Delmotte and Rubio, *Carbon,* 40:1729-1734, 2002.
Silver et al., *Connect. Tissue Res.,* 43:569-580, 2002.
Stankus et al., *J. Biomed. Mater. Res.,* 70A: 603-614, 2004.
Tan and Resasco, *J. Phys. Chem. B,* 109:14454-14460, 2005.
Tanzi et al., *J. Biomed. Mater. Res.,* 36:550-559, 1997.
West and Harner, *J. Am. Acad. Orthop. Surg.,* 2005; 13:197-207, 2005.
Wnek et al., *Nano Lett.,* 3:213-216, 2003.
Yoshimoto et al., *Biomaterials,* 24:2077-2082, 2003.
Zhong et al., *J. Biomed. Mater. Res.,* 79A:456-463, 2006.

What is claimed is:

1. A prosthetic ligament or tendon comprising:
    a sterile, biocompatible multifilament comprising a plurality of ligament- or tendon-mimicking (LTM) nanofibers having a secondary structure, the multifilament exhibiting one or more properties selected from the group consisting of:
        (a) a Young modulus of about 0.1-3000 MPa;
        (b) a tensile strength value of about 10-100 MPa;
        (c) a cross-sectional area of about 1-150 mm$^2$;
        (d) a stiffness of about 50-1000 N/mm; and
        (e) an ultimate tensile load of about 1000-6000 N.

2. The prosthetic ligament or tendon of claim 1, where the secondary structure comprises one or more crimping angles in each of at least a portion of the plurality of LTM nanofibers.

3. The prosthetic ligament or tendon of claim 2, where at least a portion of the crimping angles are between about 3 degrees and about 25 degrees.

4. The prosthetic ligament or tendon of claim 3, where the at least a portion of the crimping angles are between about 6 degrees and about 10 degrees.

5. The prosthetic ligament or tendon of claim 3, where the at least a portion of the crimping angles are between about 13 and about 17 degrees.

6. The prosthetic ligament or tendon of claim 1, where the multifilament comprises a helically wound tubular structure, and where the secondary structure comprises a plurality of overlapping nanofiber crossings each having a crossing angle.

7. The prosthetic ligament or tendon of claim 6, where the crossing angles of at least a portion of the nanofiber crossings are between about 3 degrees and about 25 degrees.

8. The prosthetic ligament or tendon of claim 1, where the LTM nanofibers comprise a polymer selected from the group consisting of elastane, hydrophilic thermoplastic polyurethane elastomer, thermoplastic polyether urethane, and segmented polyether urethane.

9. The prosthetic ligament or tendon of claim 1, where each of at least a portion of the plurality of LTM nanofibers further comprises a carbon nanoparticle.

10. The prosthetic ligament or tendon of claim 9, where the carbon nanoparticle is further defined as a chemically functionalized carbon nanoparticle.

11. The prosthetic ligament or tendon of claim 9, where the carbon nanoparticle is further defined as a carbon nanofiber (CNF).

12. The prosthetic ligament or tendon of claim 11, where the CNF is a chemically functionalized CNF, further defined as an oxidized CNF.

13. The prosthetic ligament or tendon of claim 9, where the carbon nanoparticle is further defined as a carbon nanotube (CNT).

14. The prosthetic ligament or tendon of claim 1, where the multifilament exhibits a Young modulus less than about 500 MPa.

15. The prosthetic ligament or tendon of claim 14, where the multifilament exhibits a Young modulus less than about 20 Mpa.

16. The prosthetic ligament or tendon of claim 14, where the multifilament exhibits a tensile strength between about 39 MPa and about 60 MPa.

* * * * *